(12) United States Patent
Vendely

(10) Patent No.: US 8,480,560 B2
(45) Date of Patent: Jul. 9, 2013

(54) IMPLANTABLE MEDICAL PORT WITH FLUID CONDUIT RETENTION SLEEVE

(75) Inventor: Michael J. Vendely, Lebanon, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 326 days.

(21) Appl. No.: 12/917,544

(22) Filed: Nov. 2, 2010

(65) Prior Publication Data

US 2012/0109068 A1    May 3, 2012

(51) Int. Cl.
*A61M 39/00* (2006.01)
*A61M 39/02* (2006.01)
*A61F 2/02* (2006.01)
*A61F 2/48* (2006.01)

(52) U.S. Cl.
USPC .................................. 600/37; 604/288.01

(58) Field of Classification Search
USPC ................ 600/37, 29–31; 128/912, 897–899; 604/288.01, 288.02, 502, 535
See application file for complete search history.

(56) References Cited

U.S. PATENT DOCUMENTS

| | | | |
|---|---|---|---|
| 4,476,757 A | | 10/1984 | Morris |
| 4,929,236 A | * | 5/1990 | Sampson ...................... 604/175 |
| 6,067,991 A | | 5/2000 | Forsell |
| 6,461,292 B1 | | 10/2002 | Forsell |
| 6,470,892 B1 | | 10/2002 | Forsell |
| 7,351,240 B2 | | 4/2008 | Hassler, Jr. et al. |
| 7,390,294 B2 | | 6/2008 | Hassler, Jr. |
| 7,416,528 B2 | | 8/2008 | Crawford et al. |
| 7,442,165 B2 | | 10/2008 | Forsell |
| 7,594,910 B2 | | 9/2009 | Butts et al. |
| 7,621,863 B2 | | 11/2009 | Forsell |
| 7,632,263 B2 | | 12/2009 | Denoth et al. |
| 7,699,770 B2 | | 4/2010 | Hassler, Jr. et al. |
| 7,775,215 B2 | | 8/2010 | Hassler, Jr. et al. |
| 7,850,660 B2 | | 12/2010 | Uth et al. |
| 2006/0199997 A1 | | 9/2006 | Hassler, Jr. et al. |
| 2006/0211914 A1 | * | 9/2006 | Hassler et al. .................. 600/37 |
| 2006/0264911 A1 | * | 11/2006 | Nelson ....................... 604/890.1 |
| 2007/0123831 A1 | | 5/2007 | Haindl et al. |
| 2008/0114308 A1 | | 5/2008 | Di Palma et al. |
| 2008/0287867 A1 | | 11/2008 | Yow et al. |
| 2010/0121313 A1 | * | 5/2010 | Goode et al. .................. 604/535 |
| 2011/0251453 A1 | * | 10/2011 | Honaryar et al. ............... 600/37 |

FOREIGN PATENT DOCUMENTS

| | | |
|---|---|---|
| EP | 0 343 910 | 11/1989 |
| GB | 2 090 639 | 7/1982 |

OTHER PUBLICATIONS

International Search Report dated Mar. 19, 2012 for Application No. PCT/US2011/058738.

* cited by examiner

*Primary Examiner* — Charles A Marmor, II
*Assistant Examiner* — Shannon Canty
(74) *Attorney, Agent, or Firm* — Frost Brown Todd LLC

(57) ABSTRACT

A surgically implantable medical port has a housing with a fluid reservoir therein, a tubular stem extending away from the housing, a fluid conduit mounted on the stem, and a plurality of cantilevered fingers having free ends that are pressed against the fluid conduit in order to prevent conduit detachment from the port. The cantilevered fingers may be provided in a retention sleeve positioned about the fluid conduit. The retention sleeve may be unitarily formed with the housing of the port. The retention sleeve may be formed by at least two separate pieces, such as sections that pivot open and closed relative to the housing and that snap together in a closed position.

14 Claims, 12 Drawing Sheets

IMPLANTABLE MEDICAL PORT WITH FLUID CONDUIT RETENTION SLEEVE

BACKGROUND

Implantable medical devices may be implanted in a patient to perform a therapeutic function for that patient. Non-limiting examples of such devices include pace makers, access ports (such as vascular access ports, infusion ports, and ports used with gastric band systems, etc.) and gastric pacing devices. Such implants may need to be attached, perhaps subcutaneously, in an appropriate place in order to function properly. It may be desirable that the procedure to implant such devices be quick, easy and efficient.

Ports may be placed beneath the skin of a body for injecting fluids into or withdrawing fluids from the body. By way of example, vascular access ports may be used for infusing medication, blood draws, and many other applications. Injection ports may be used for adding or withdrawing fluid in adjustable gastric band systems. These various access ports may include an implantable port housing coupled to a fluid conduit which delivers fluid to or withdraws fluid from a location in the patient's body (e.g., a vein or a gastric band, etc.).

Gastric band systems are operable to restrict the flow of food from the esophagus into the stomach. Some gastric bands include a fluid-filled elastomeric bladder with fixed endpoints that encircles the stomach just inferior to the gastro-esophageal junction. When fluid is added to the bladder, the band expands against the stomach, creating a food intake restriction or stoma in the stomach. To decrease this restriction, fluid is removed from the bladder. Examples of gastric bands are disclosed in U.S. Pat. No. 7,416,528, entitled "Latching Device for Gastric Band," issued Aug. 26, 2008, the disclosure of which is incorporated by reference herein. Another example of such an adjustable gastric band is disclosed in U.S. Pat. No. 6,067,991, entitled "Mechanical Food Intake Restriction Device," issued May 30, 2000, the disclosure of which is incorporated by reference herein.

To the extent that an adjustable gastric band system includes an injection port configured to receive the needle of a syringe assembly in order to add or withdraw fluid to or from the gastric band, those of ordinary skill in the art will appreciate that it may be desirable in some settings to locate both the injection port and, more specifically, the center of the injection port (e.g., when the septum of the injection port is at the center of the injection port). Locating the approximate center of the injection port with some degree of accuracy may facilitate addition or withdrawal of fluid via the injection port to adjust the gastric band system. One example of a system and method for identifying the location of an injection port is disclosed in U.S. Pub. No. 2006/0211914, entitled "System and Method for Determining Implanted Device Positioning and Obtaining Pressure Data" published Sep. 21, 2006, and issued Aug. 17, 2010 as U.S. Pat. No. 7,775,215, the disclosure of which is incorporated by reference herein.

Those of ordinary skill in the art will appreciate that it may be advantageous in certain circumstances to sense pressure, strain, and/or other parameters associated with operation of a gastric band device. In some settings, it may be desirable to obtain data indicative of the pressure of fluid in a gastric band. Various examples of methods and devices for obtaining pressure data and other types of data are disclosed in U.S. Pub. No. 2006/0189888, entitled "Device for Non-Invasive Measurement of Fluid Pressure in an Adjustable Restriction Device," published Aug. 24, 2006, and issued Apr. 20, 2010 as U.S. Pat. No. 7,699,770, the disclosure of which is incorporated by reference herein. Additional examples of methods and devices for obtaining pressure data and other types of data are disclosed in U.S. Pub. No. 2006/0199997, entitled "Monitoring of a Food Intake Restriction Device," published Sep. 7, 2006, and issued Sep. 13, 2011 as U.S. Pat. No. 8,016,745, the disclosure of which is incorporated by reference herein.

Such parameter data may be obtained before, during, and/or after adjustment of a gastric band, and may be useful for adjustment, diagnostic, monitoring, or other purposes, and may also be obtained with respect to a mechanically actuated gastric band. In settings where a fluid-filled gastric band is used, pressure data may be used to determine whether the amount of fluid in the gastric band needs to be adjusted; and/or for other purposes.

While a variety of implantable access ports and gastric band systems have been made and used, it is believed that no one prior to the inventor(s) has made or used an invention as described herein.

BRIEF DESCRIPTION OF THE DRAWINGS

While the specification concludes with claims which particularly point out and distinctly claim the invention, it is believed the present invention will be better understood from the following description of certain examples taken in conjunction with the accompanying drawings, in which like reference numerals identify the same elements and in which:

Figure 1:
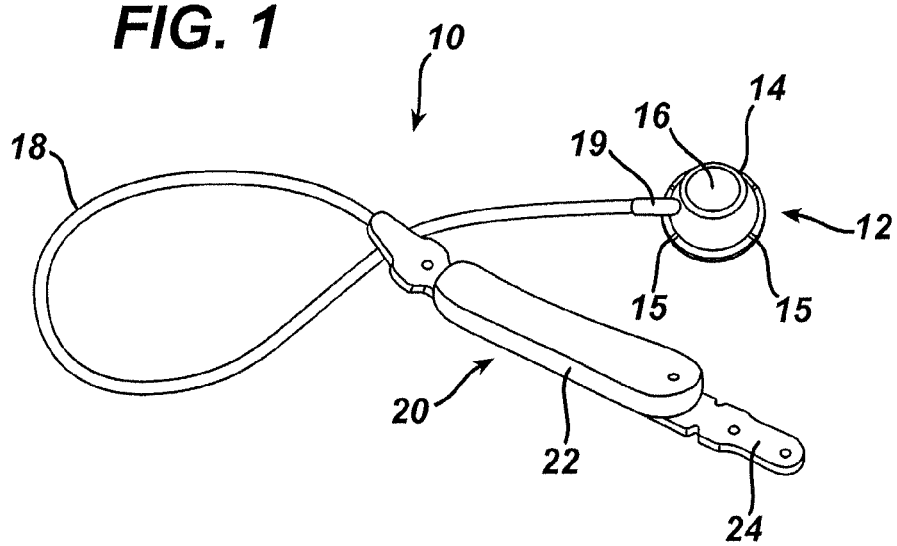
FIG. 1 depicts a perspective view of an implantable portion of an exemplary gastric band system, including an injection port having an integral fluid conduit retention sleeve.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. For example, while various embodiments of ports having tissue in-growth promoting surfaces and/or features are depicted and described as being part of a gastric band system, the tissue in-growth surfaces and features may be employed with other types of implantable medical ports or other medical devices. Accordingly, the drawings and descriptions should be regarded as illustrative in nature and not restrictive.

I. Exemplary Gastric Band System

FIGS. 1-4 illustrate an exemplary gastric band system (10). As shown, gastric band system (10) comprises an injection port (12), a gastric band (20), and a flexible conduit (or catheter) (18). Injection port (12) of the present example comprises a port housing (14), a needle penetrable septum (16) and a fluid reservoir (not shown in FIGS. 1-4) located beneath septum (16). Catheter (18) (e.g., a flexible and/or resilient polymeric tube) is attached to port housing (14) and is in fluid communication with the fluid reservoir therein. A needle may pierce septum (16) to reach the reservoir and add or withdraw fluid (e.g., saline, etc.), as described in greater detail below.

Port housing (14) may comprise a unitary structure (e.g., a one piece housing insert molded about septum (16)). Alternatively, port housing (14) may be assembled from two or more mating components such as a port body which at least partially receives a port base therein (as further described herein). Injection port (12) also includes a retention sleeve (19), which extends about a portion of fluid conduit (18) where conduit (18) is attached to housing (14). Port housing (14) may be formed of titanium, plastic, or any other suitable material or combination of materials. Septum (16) may be formed of silicone or any other suitable material or combination of materials.

Injection port (12) may be subcutaneously secured over a patient's sternum, to the patient's abdominal fascia, or in any other suitable location. By way of example, port (12) may be sutured in place using the suture apertures (15) located about the periphery of port housing (14). In other versions, injection port (12) may be configured and operable in accordance with the teachings of U.S. Pub. No. 2005/0283118, entitled "Implantable Medical Device with Simultaneous Attachment Mechanism and Method," published Dec. 22, 2005, and issued Dec. 14, 2010 as U.S. Pat. No. 7,850,660, the disclosure of which is incorporated by reference herein. For example, injection port (12) may be configured to include a plurality of fasteners that are selectively deployed from the injection port in order to secure the port in place within a patient, as further described in U.S. Pub, No. 2005/0283118, issued as U.S. Pat. No. 7,850,660. Alternatively, injection port (12) may have any other suitable configuration and/or operability.

Gastric band (20) of the present example comprises an inflatable bladder (22) that is secured to a flexible strap (24). Inflatable bladder (22) may be formed of silicone or any other suitable material or combination of materials. Catheter (18) provides fluid communication between bladder (22) and the reservoir of injection port (12). Catheter (18) may be formed of silicone or any other suitable material or combination of materials. In the present example, catheter (18), bladder (22), and injection port (12) form a closed fluid circuit. Accordingly, a needle that is inserted through septum (16) into the underlying reservoir may be used to add fluid to or withdraw fluid from inflatable bladder (22) in order to adjust the restriction created by gastric band (20) as described in greater detail below. In some versions, gastric band (20) is configured and operable in accordance with the teachings of U.S. Pat. No. 7,416,528, entitled "Latching Device for Gastric Band," issued Aug. 26, 2008, the disclosure of which is incorporated by reference herein. Alternatively, gastric band (20) may have any other suitable configuration and/or operability.

Figure 2:
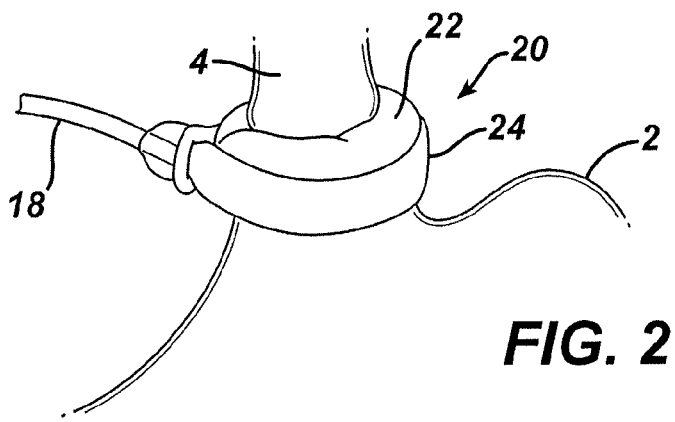
FIG. 2 depicts a perspective view of the gastric band of FIG. 1, showing the band positioned around the gastro-esophageal junction of a patient.

In some settings, gastric band (20) is applied about the gastro-esophageal junction of a patient. In particular, and as shown in FIG. 2, gastric band (20) is installed such that bladder (22) is adjacent to the tissue of the gastro-esophageal junction, with strap (24) on the outside of bladder (22). The ends of strap (24) are secured relative to each other when gastric band (20) is sufficiently wrapped about the patient's stomach (2). While strap (24) is flexible in this example, strap (24) substantially resists stretching along its length. Accordingly, when fluid is added to bladder (22) (e.g., using a needle inserted through septum (16) of injection port (12), etc.), bladder (22) expands and exerts inward forces on the gastro-esophageal junction of the patient. This reduces the size of the internal stoma at the gastro-esophageal junction, thereby creating a restriction on food intake into the patient's stomach (2). It should be understood that the size of this stoma may be decreased by adding more fluid to bladder (22) to create a greater degree of restriction, or increased by withdrawing fluid from bladder (22) to reduce the degree of restriction.

Figure 3:
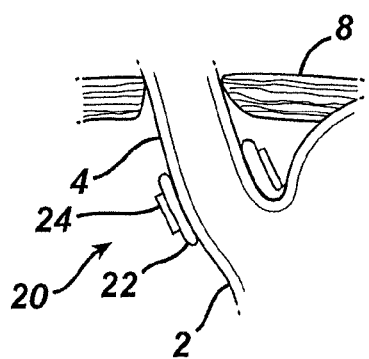
FIG. 3 depicts a cross-sectional view of the gastric band of FIG. 1, showing the band positioned around the gastro-esophageal junction of a patient in a deflated configuration.
Figure 4:
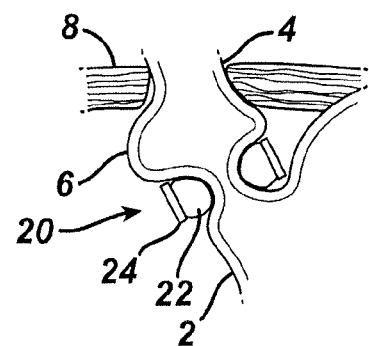
FIG. 4 depicts a cross-sectional view of the gastric band of FIG. 1, showing the band positioned around the gastro-esophageal junction of a patient in an inflated configuration to create a food intake restriction.

As shown in FIGS. 2-4, an installed gastric band (20) at least substantially encloses the upper portion of stomach (2) near the junction with esophagus (4) in the present example. FIG. 3 shows gastric band (20) in a deflated configuration, where bladder (22) contains little to no fluid, thereby maximizing the size of the stoma opening into stomach (2). FIG. 4 shows gastric band (20) in an inflated, fluid-filled configuration, where bladder (22) contains substantially more fluid than is shown in FIG. 3. In this configuration shown in FIG. 4, the pressure of gastric band (20) against stomach (2) is increased due to the fluid within bladder (22), thereby decreasing the stoma opening to create a food intake restriction. FIG. 4 also schematically illustrates the dilation of esophagus (4) above gastric band (20) to form an upper pouch (6) beneath the diaphragm muscle (8) of the patient.

As mentioned previously, injection port (12) may be subcutaneously secured over a patient's sternum, to the patient's abdominal fascia, or in any other suitable location. In some versions of a gastric band system, catheter (18) may become inadvertently detached from injection port (12), thus allowing fluid to leak from bladder (22) and the fluid reservoir within injection port (12). As further described herein, retention sleeve (19) includes a plurality of cantilevered, flexible fingers that urge catheter (18) against a tubular stem extending from housing (14), thereby substantially preventing catheter (18) from becoming disconnected from housing (14) after implantation. (The cantilevered fingers and tubular stem are not shown in FIG. 1.) While retention sleeve (19) is shown in FIG. 1 as being an integral part of housing (14), in other versions the retention sleeve is a separate component (or plurality of components) attached to the port housing (14).

II. Injection Port with Integral Conduit Retention Sleeve

FIGS. 5-11 show an exemplary alternative injection port (26) suitable for use, for example, as part of gastric band system (10). Although a conduit retention feature is illustrated in the drawings as being embodied in or associated with an injection port (26) for use as part of a gastric band system (10), the conduit retention features described herein may be used with any implantable medical device for which it is suited, including by way of example only other types of implantable medical ports (e.g., vascular access ports, etc.) and gastric pacing devices. Injection port (26) of the present example is similar in construction to injection port (12) in FIG. 1, and includes an integral retention sleeve (58). It should be noted, however, that injection port (26) may be configured similar to the port depicted and described in U.S. Pub. No. 2005/0283118, with the addition of a conduit retention feature as further described herein.

Injection port (26) includes septum (28), as well as a port housing comprising port base (30) (see FIG. 8) and port body (32). Port base (30) includes a generally cup-shaped portion defined by cylindrical sidewall (34) and bottom (36). Septum (28) is positioned atop sidewall (34) of port base (30) such that the cup-shaped portion of port base (30) and the bottom surface of septum (28) define a fluid reservoir (38). Port base (30) is also configured to nest within port body (32) such that septum (28) is compressed between cylindrical sidewall (34) of port base (30) and an annular rim (40) on port body (32), which engages the upper surface of septum (28) about an annular portion thereof. In this fashion, fluid reservoir (38) is located directly beneath septum (28) so that a needle (e.g., Huber needle) of a syringe may be inserted into fluid reservoir (38) through septum (28). Septum (28) is sufficiently compressed between port base (30) and port body (32) so as to be adequately self-healing and thus maintain a fluid tight system under pressure even after multiple penetrations by a needle.

Injection port (26) also includes a plurality of apertures (42) arrayed about the bottom periphery of port body (32). Apertures (42) may be used to secure port (26) in a patient using sutures or other suitable fasteners. Cutouts (44) are provided above each of the apertures (42) in order to facilitate the attachment of port (26) using sutures or other fasteners. Alternatively, injection port (26) may be configured similar to that shown and described in U.S. Pub. No. 2005/0283118, and include one or more deployable fasteners housed within the injection port for securing the port subcutaneously within a patient. Of course, any other suitable components, features, and/or techniques for securing injection port (26) within a patient may be used. It will be understood that the construction of injection port (26) is merely exemplary of one possible embodiment. For example, injection port (26) may be greatly simplified to include a unitary port body (or housing) configured to retain a septum, and having a fluid reservoir (or chamber) located beneath the septum.

Septum (28) may be made of any suitable biocompatible material such as silicone. Port base (30) and port body (32) may be made of any suitable biocompatible material having sufficient stiffness and strength, such as polyether ether ketone (known as PEEK) or other plastic suitable for implantation in a patient. Port base (30) may be retained within port body (32) in any of a variety of ways. In the example shown, port base (30) is secured within port body (32) using a suitable biocompatible adhesive (e.g., isocyanate or cyanoacrylate adhesive, etc.).

Figure 6:
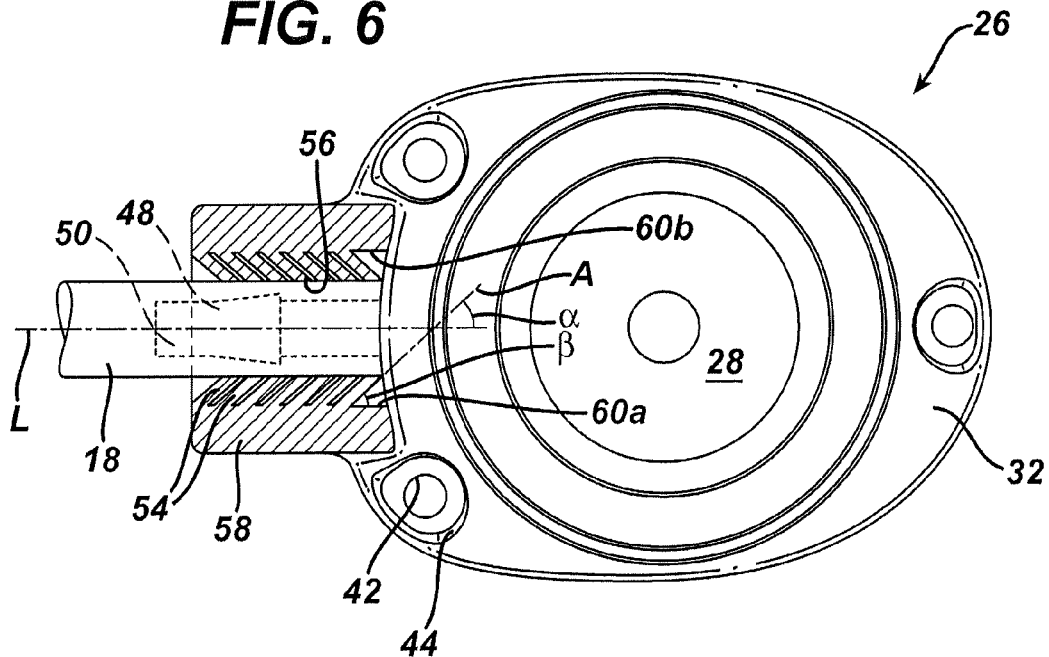
FIG. 6 depicts a top plan view of the injection port of FIG. 5, showing the retention sleeve in cross-section and the fluid conduit mounted on the stem of the injection port.

Port base (30) includes passageway (46) in fluid communication with fluid reservoir (38). Passageway (46) is defined by a tubular stem (48) extending away from sidewall (34) of port base (30). Resilient fluid conduit (or catheter) (18), which leads, for example, to adjustable gastric band (20), is connected to stem (48) so as to be in fluid communication with reservoir (38). In particular, and as best seen in FIG. 6, one end of fluid conduit (18) is press fit over the distal end (50) of tubular stem (48). Since the outer diameter of tubular stem (48) is somewhat greater than the inner diameter of conduit (18), the resilient conduit (18) will be compressed so as to provide an interference fit. A tapered barb (52) is also provided on stem (48) in order to enhance the interference fit of conduit (18) over stem (48). Of course, stem (48) may have any other suitable features and/or configurations.

While a tighter interference fit of conduit (18) over stem (48) may be provided by increasing the size difference between the outer diameter of stem (48) and inner, uncompressed diameter of conduit (18), it may become more difficult to attach conduit (18) to stem (48) as the size difference is increased. This may be problematic since surgeons may implant an injection port in a patient before attaching the fluid conduit to the port (26) and/or because at the time conduit (18) is coupled with stem (48), conduit (18) may be lubricated with bodily fluids and the surgeon's hand may be gloved, making it difficult to sufficiently grip conduit (18). In the example shown in FIGS. 5-11, a plurality of cantilevered, resilient fingers (54) are provided on injection port (26). A portion of the free distal end walls (56) of fingers (54) urge fluid conduit (18) against the stem (48).

As further described below, fingers (54) are angled inwardly toward port body (32). In this manner, fingers (54) are similar to the fingers (or "feathers") of a featherboard. An example of a featherboard in a completely different setting is disclosed in U.S. Pat. No. 4,476,757, entitled "Adjustable Featherboard," issued Oct. 16, 1984, the disclosure of which is incorporated by reference herein. In the present example, fingers (54) on injection port (26) not only urge fluid conduit (18) against stem (48) while still permitting conduit (18) to be press fit over stem (48), fingers (54) also resist movement of fluid conduit (18) away from port body (32) (e.g., to help prevent conduit (18) from being inadvertently pulled off of stem (48)).

Figure 5:
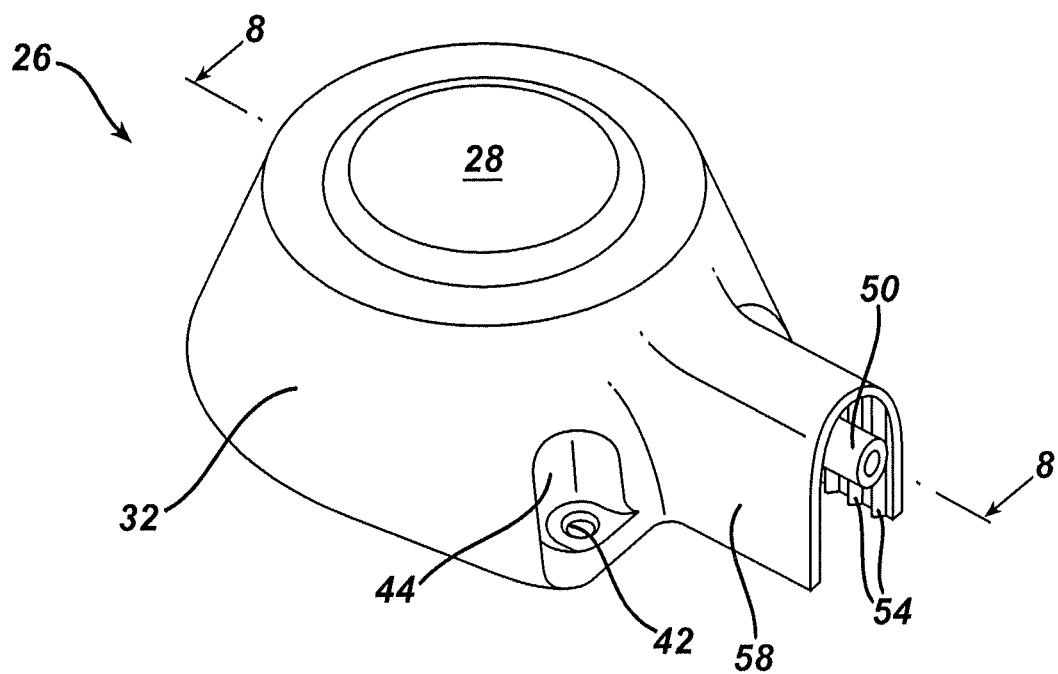
FIG. 5 depicts a perspective view of an exemplary alternative injection port, having an integral fluid conduit retention sleeve.

As shown in FIG. 5, cantilevered fingers (54) are provided along the interior of retention sleeve (58), which extends partially along and around stem (48). In the present example, retention sleeve (58) extends along either side and over stem (48), and generally has an arch-shaped or U-shaped cross-section. Of course, a variety of other shapes for retention sleeve (58) may be employed. Retention sleeve (58) is also formed integral with port body (32)—i.e., retention sleeve (58) is simply an extension of port body (32), which may be formed, for example, by molding port body (32) so as to include retention sleeve (58). Of course, retention sleeve may be provided in any of a variety of alternative configurations, such as a separate structure that is attached to port body (32) (or another part of the injection port housing) either before or after conduit (18) is fit over stem (48). A separate retention sleeve (58) may be attached to port body (32) (and/or another part of the injection port housing) in any of a variety of ways such as using a biocompatible adhesive, fasteners (e.g., threaded fasteners), snap fittings, and in other ways as will be apparent to those skilled in the art in view of the teachings herein.

In the present example, cantilevered fingers (54) extend in two sets from the interior sidewalls (60a, 60b) of retention sleeve (58), with the two sets of fingers (54) arranged along opposite sides of stem (48). Thus, a first set of cantilevered fingers (54) extends away from sidewall (60a), and a second set of cantilevered fingers (54) extends away from sidewall (60b). Any number, length, sets, and arrangement of cantilevered fingers (54) may be provided, and that shown is merely one example. The cantilevered fingers (54) of each set, in their undeflected state shown in FIGS. 6 and 7, extend away from sidewalls (60a, 60b) generally parallel to one another (i.e., the fingers (54) of the first set extend parallel to one another, and the fingers (54) of the second set extend parallel to one another).

The fingers (54) are also angled in the direction of port body (32) (i.e., away from the distal end (50) of stem (48)), rather than being perpendicular with respect to the longitudinal axis L of stem (48). Thus, as shown in FIG. 6, an extended line A drawn parallel to fingers (54) in the cross-sectional plane of FIG. 6 intersects the longitudinal axis L of stem (48) at an angle α, which is less than 90 degrees in the present example. By way of example only, angle α may be between approximately 30 degrees (inclusive) and approximately 50 degrees (inclusive). If sidewalls (60a, 60b) are parallel to the longitudinal axis L of stem (48), angle α will be equivalent to angle β between fingers (54) and sidewall (60a, 60b). By angling fingers (54) away from the distal end (50) of stem (48), cantilevered fingers (54) of the present example will substantially resist detachment of fluid conduit (18) from stem (48) in the manner described below.

Figure 9:
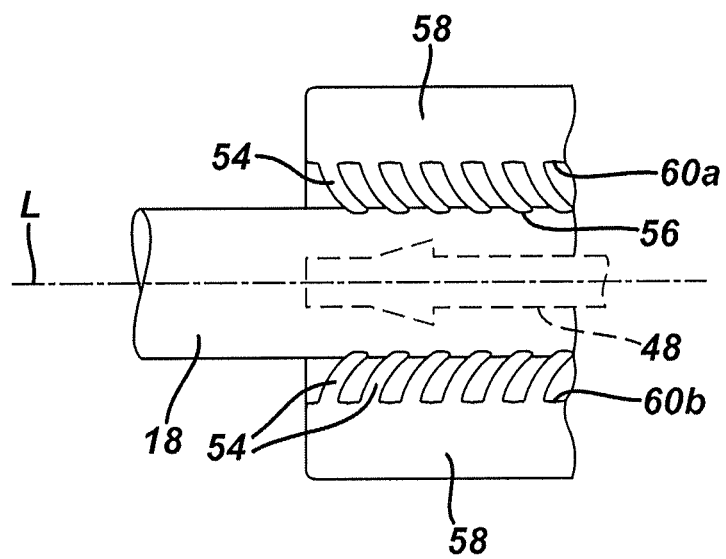
FIG. 9 depicts a partial bottom plan view of the retention sleeve portion of the injection port of FIG. 5, with the fluid conduit mounted on the stem of the injection port.
Figure 10:
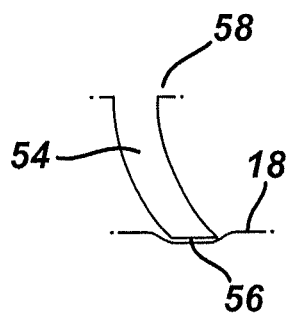
FIG. 10 depicts a schematic view of a cantilevered finger of the retention sleeve portion of the injection port of FIG. 5, where the finger has been deformed by the fluid conduit.

The free distal end surfaces (56) of cantilevered fingers (54) are spaced away from stem (48) such that, as one end of fluid conduit (18) is slid over the distal end (50) of stem (48) to mount the conduit (18) on the stem (48), the fingers (54) are resiliently deformed (i.e., flexed) inwardly away from distal end (50) of stem (48), as best seen in FIGS. 9 and 10. This inward deflection causes the free distal end surfaces (56) of flexible fingers (54) to exert an opposing force against the outer surface of the conduit (18), thereby pressing resilient conduit (18) against stem (48) and substantially preventing detachment of conduit (18). Fingers (54) are configured in terms of their length, width, thickness, resilience, and material so as to flex sufficiently to allow conduit (18) to be readily slid onto stem (48) while also exerting sufficient force against the outer surface of conduit (18) to substantially resist detachment of the conduit from stem (48).

Figure 7:
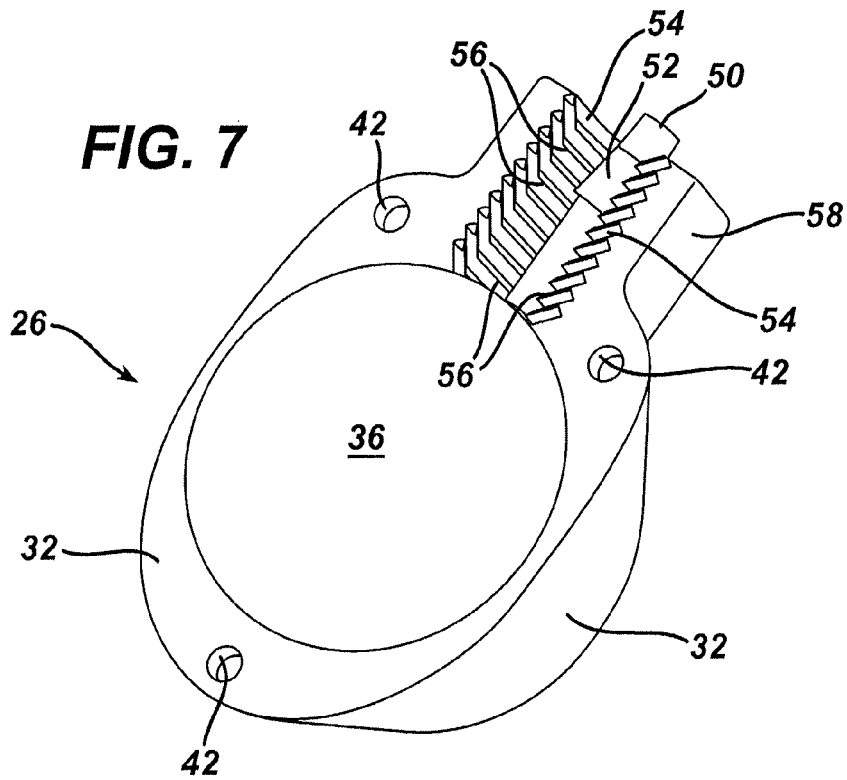
FIG. 7 depicts a bottom perspective view of the injection port of FIG. 5.
Figure 8:
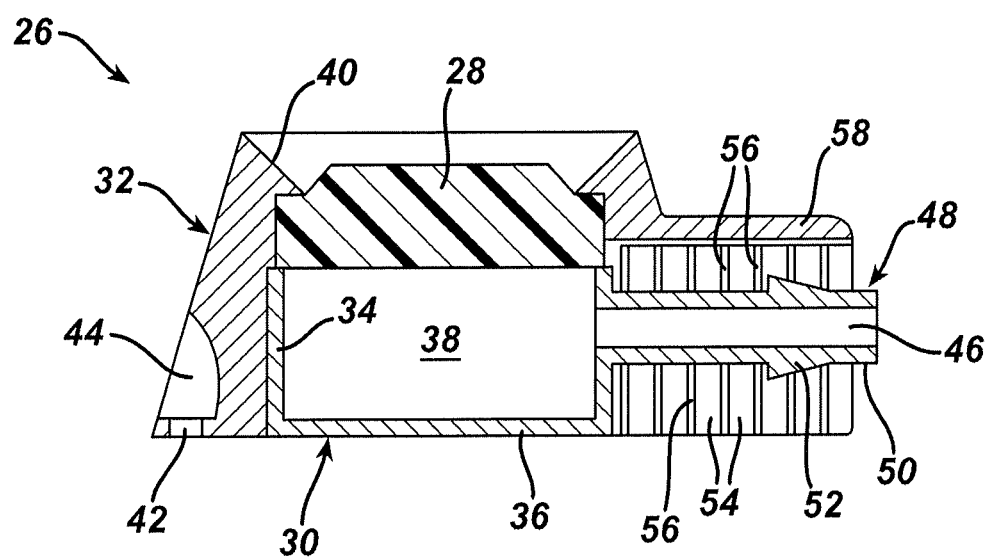
FIG. 8 depicts a cross-sectional view of the injection port of FIG. 5, taken long line 8-8 of FIG. 5.

The free distal end surfaces (56) of fingers (54) may extend parallel to the longitudinal axis L of stem (48) when fingers (54) are in their undeformed state (FIG. 7). In the present example, however, distal end surfaces (56) are angled slightly with respect to longitudinal axis L of stem (48) when fingers (54) are in their undeformed state such that, when fingers (54) are deformed inwardly (inwardly toward port body (32) and outwardly away from longitudinal axis L) by conduit (18), the distal end surfaces (56) will generally be parallel to longitudinal axis L (as shown in FIGS. 9 and 10). In this manner, the entire surface area of distal end surfaces (56) in contact with conduit (18) will exert an opposing force thereon. While the fingers (54) of the embodiment shown in FIGS. 5-11 are generally all of the same length, fingers (54) may be of varying lengths. For example, the fingers (54) nearest distal end (50) of stem (48) may be shorter than those located furthest away in order to facilitate the fitting of conduit (18) over the stem (48). It should also be pointed out that, while distal end surfaces (56) of fingers (54) may be rounded or have any of a variety of other shapes, the generally flat, angled end surface (56) shown in FIGS. 10 and 11 may provide an angular trailing edge (62) that helps further prevent detachment of conduit (18), as further described below.

Flexible fingers (54) not only help retain conduit (18) on stem (48) by exerting an opposing force against conduit (18), they also retain conduit (18) on stem (48) by inhibiting movement of conduit (18). When a force is exerted on conduit (18) pulling conduit (18) away from stem (48) (i.e., in the direction of the arrow shown in FIG. 11), friction between distal end surface (56) and the outer surface of conduit (18) will result in fingers (54) being pulled in the same direction. As fingers (54) are pulled in the direction of the arrow in FIG. 11, the fingers (54) will be returned toward their undeformed state. This results in the distal end surfaces (56) of fingers (54), particularly trailing edges (62), being further urged against the outer surface of fluid conduit (18). Angular trailing edge (62), in particular, will dig into the outer surface of resilient conduit (18) and substantially prevent conduit (18) from becoming detached from stem (48). While angular trailing edge (62) is depicted in the example as having a sharp corner for digging into conduit (18), angular trailing edge (62) may be slightly rounded so that trailing edge (62) will not cut or damage conduit (18) when conduit (18) is pulled in a direction away from injection port (26).

It should also be noted that the retention sleeve (58) does not extend over the entire length of stem (48) in the present example. Thus, as seen in FIG. 5, the distal end (50) of the stem is located outside of the retention sleeve (58). This arrangement may facilitate press fitting of conduit (18) over stem (48). Alternatively, retention sleeve (58) may extend over at least the entire length of stem (48) in some other versions.

In the present example, cantilevered fingers (54) provided in retention sleeve (58) attached to port housing (32) are depicted as having generally straight, parallel sidewalls, such that, in the example shown in FIGS. 5-11, an elongate, straight slot is provided between adjacent fingers (54). Alternatively, fingers (54) may have curved sidewalls that are still angled away from the distal end of stem (48) such that fluid conduit (18) urges the free distal ends of fingers (54) radially away from stem (48) and conduit (18) when conduit (18) is slid over stem (48); and pulls the distal ends of the fingers into conduit (18) when the conduit (18) is pulled away from injection port (26). Other suitable components, features, and configurations that may be incorporated into injection port (26) will be apparent to those of ordinary skill in the art in view of the teachings herein.

III. Injection Port with Separate Conduit Retention Sleeve Attached to Port

Figure 12:
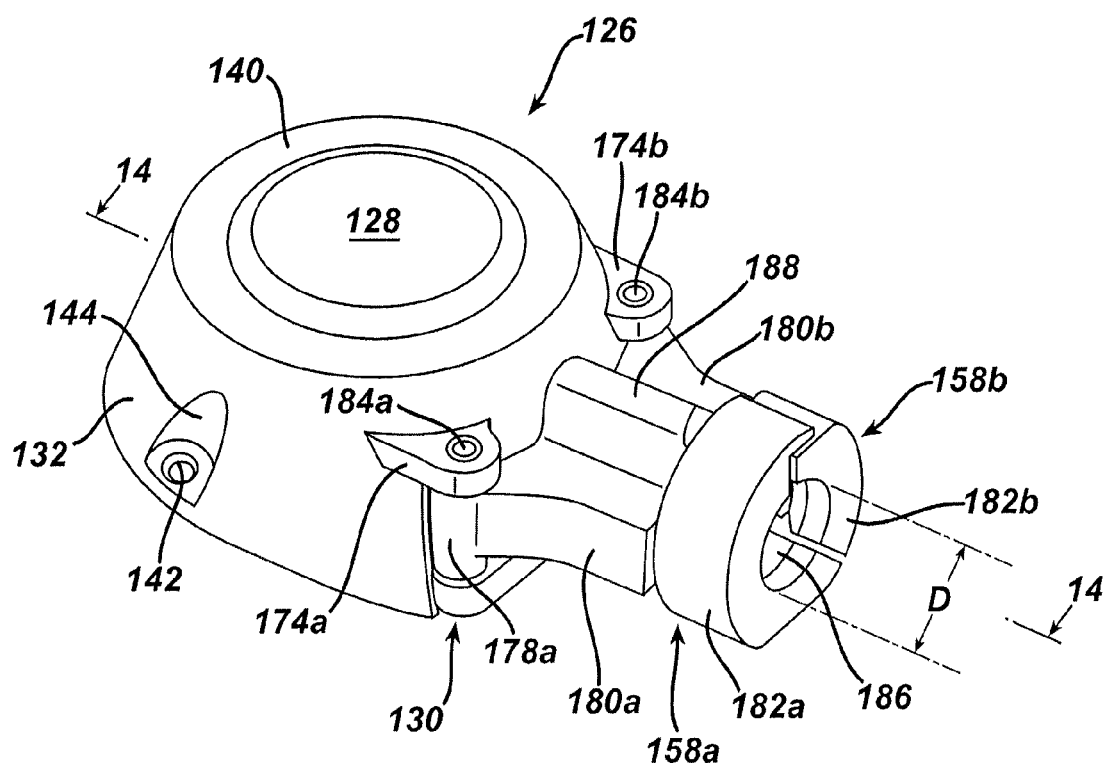
FIG. 12 depicts a perspective view of another exemplary alternative injection port, having a two piece conduit retention sleeve.
Figure 13:
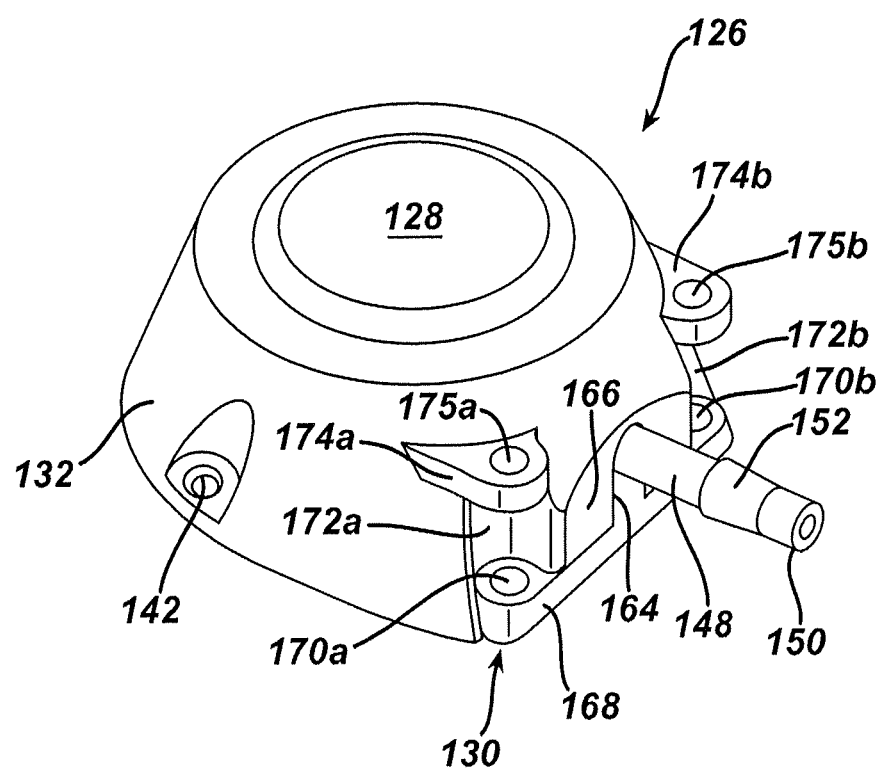
FIG. 13 depicts a perspective view of the injection port of FIG. 12, with the two piece retention sleeve removed.
Figure 14:
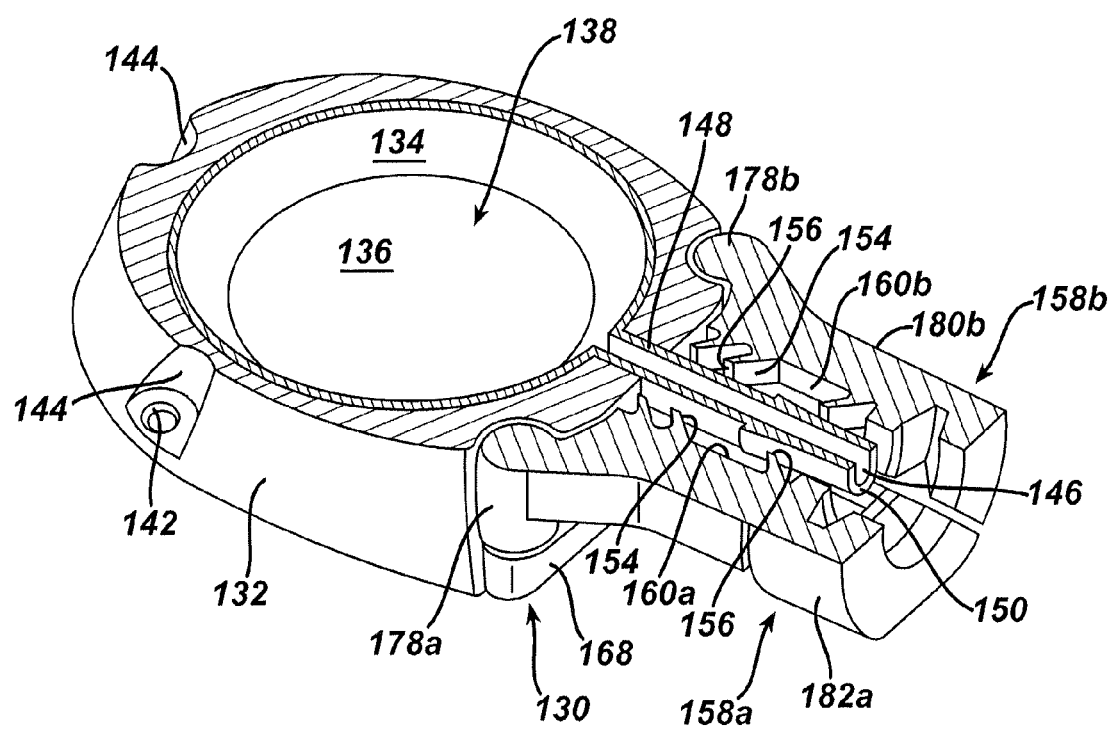
FIG. 14 depicts perspective cross-sectional view of the injection port of FIG. 12, taken along line 14-14 of FIG. 12.

FIGS. 12-14 depict another exemplary alternative injection port (126) having a plurality of flexible, cantilevered fingers provided in a retention sleeve (158) for retaining a fluid conduit (18) that is operatively attached to injection port (126). Once again, although the conduit retention feature is illustrated in the figures as being associated with an injection port (126) for use as part of a gastric band system (10), the conduit retention features on port (126) may be used with any implantable medical device for which it is suited, including by way of example only other types of implantable medical ports (e.g., vascular access ports, etc.) and gastric pacing devices.

Injection port (126) is similar in construction to injection port (26) in FIG. 5, apart from the configuration of the retention sleeve (158), which comprises a pair of mating sections (158a, 158b) pivotally attached to the port housing. It should be noted, however, that injection port (126) may be configured similar to the port depicted and described in U.S. Pub. No. 2005/0283118, with the addition of the conduit retention sleeve (158) further described below. It should also be understood that, while two mating sections (158a, 158b) are used in the present example, any other suitable number of mating sections may be used. By way of example only, three or more mating sections may be selectively moved inwardly and outwardly relative to a central region, similar to components of a conventional drill chuck. Other suitable configurations will be apparent to those of ordinary skill in the art in view of the teachings herein.

Injection port (126) includes septum (128), as well as a port housing comprising port base (130) and port body (132). Port base (130) includes a generally cup-shaped portion defined by cylindrical sidewall (134) and bottom (136). Septum (128) is positioned atop sidewall (134) of port base (130) such that the cup-shaped portion of port base (130) and the bottom surface of septum (128) define a fluid reservoir (138). Port base (130) is also configured to nest partially within port body (132) such that septum (128) is compressed between cylindrical sidewall (134) of port base (130) and an annular rim (140) on port body (132), which engages the upper surface of septum (128) about an annular portion thereof. In this fashion, fluid reservoir (138) is located directly beneath septum (128) so that a needle may be inserted into fluid reservoir (138) through septum (128). Septum (128) is sufficiently compressed between port base (130) and port body (132) so as to be adequately self-healing and thus maintain a fluid tight system under pressure even after multiple penetrations by a needle.

Injection port (126) also includes a plurality of apertures (142) arrayed about the bottom periphery of port body (132), Apertures (142) may be used to secure port (126) in a patient using sutures or other suitable fasteners. Cutouts (144) are provided above each of the apertures (142) in order to facilitate the attachment of port (126) using sutures or other fasteners. Alternatively, injection port (126) may be configured similar to that shown and described in U.S. Pub. No. 2005/0283118, and include one or more deployable fasteners housed within the injection port for securing the port subcutaneously within a patient. Of course, any other suitable components, features, and/or techniques for securing injection port (126) within a patient may be used.

Septum (128) may be made of any suitable biocompatible material such as silicone. Port base (130) and port body (132) may be made of any suitable biocompatible material having sufficient stiffness and strength, such as polyether ether ketone (known as PEEK) or other plastic suitable for implantation in a patient. Port base (130) may be retained within port body (132) by any of a variety of ways. In the example shown, port base (130) is secured within port body (132) using a suitable biocompatible adhesive (e.g., isocyanate or cyanoacrylate adhesive, etc.).

Port base (130) includes passageway (146) in fluid communication with fluid reservoir (138). Passageway (146) is defined by a tubular stem (148) extending away from sidewall (134) of port base (130). A resilient fluid conduit (or catheter) which leads, for example, to adjustable gastric band (20), may be connected to stem (148) so as to be in fluid communication with reservoir (138). In particular, one end of the fluid conduit may be press fit over the distal end (150) of tubular stem (148) in the manner described previously with respect to port (26) and conduit (18). The outer diameter of tubular stem (148) is somewhat greater than the inner diameter of the conduit such that the resilient conduit will be compressed so as to provide an interference fit. A tapered barb (152) is also provided on stem (148) in order to enhance the interference fit of a conduit over stem (148). Of course, stem (148) may have any other suitable features and/or configurations.

Port base (130) is positioned partially within port body (132) such that tubular stem (148) extends out of port body (132) through an opening (164) provided in a distal end face (166) of port body (132) (see FIG. 13). Port base (130) also includes a flange (168) positioned beneath distal end face (166) of port body (130). Flange (168) includes a pair of apertures (170a, 170b) located adjacent either side distal end face (166). Semicylindrical grooves (172a, 172b) are provided in port body (132), and are located on opposite sides of stem (148) directly above apertures (170a, 170b) in port base (130). In addition, a pair of pivot shoulders (174a, 174b) are provided on port body (132), and are also located on either side of stem (148) above grooves (172a, 172b). Apertures (176a, 176b) are provided in pivot shoulders (174a, 174b) and are axially aligned with apertures (170a, 170b), respectively, in flange (168) of port base (130).

First and second retention sleeve sections (158a, 158b) each have a pivot barrel (178a, 178b) at a proximal end, a finger support section (180a, 180b) extending distally away from the pivot barrel (178a, 178b), and a head portion (182a, 182b) at the distal end of the finger support section (180a, 180b). The first and second retention sleeve sections (158a, 158b) are configured to matingly engage each other to form a generally tubular sleeve that substantially surrounds stem (148). Pivot pins (184a, 184b) extend away from the upper surface of pivot barrels (178a, 178b). Similar pivot pins also extend away from the bottom surface of pivot barrels (178a, 178b).

First and second retention sleeve sections (158a, 158b) are pivotally mounted to the injection port housing by trapping the pivot pins on barrels (178a, 178b) in apertures (170, 176) on port base (130) and port body (132), respectively, with pivot barrels (178a, 178b) rotatably supported within grooves (172a, 172b) for pivotal movement. Retention sleeve sections (158a, 158b) are mounted to the port housing before port base (130) is inserted into port body (132). In particular, pivot pins (184a, 184b) are inserted into apertures (176a, 176b), respectively, on port body (132). Thereafter, the cup-shaped portion of port base (130), which helps define reservoir (138), is inserted into port body (132) though the open bottom of port body (132). At the same time, the pivot pins extending from the bottom of barrels (178a, 178b) are inserted into apertures (170a, 170b) on port base (130). Port base (130) is then secured to port body (132) (e.g., using an adhesive), while the pivot pins remain free to rotate within their respective apertures (170, 176). In this manner, first and second retention sleeve sections (158a, 158b) are free to pivot about an axis extending through pivot pins (174a, 174b). Of course retention sleeve sections (158a, 158b) may be pivotally attached to the port housing in a variety of alternative ways. For example, in place of pivot pins on barrels (178a, 178b), axles fixedly positioned between apertures (170) and (174) may extend through longitudinal apertures in barrels (178a, 178b) such that the barrels are free to rotate about the axles. Other suitable ways in which retention sleeve sections (158a, 158b) may be coupled with the port housing will be apparent to those of ordinary skill in the art in view of the teachings herein.

Figure 15:
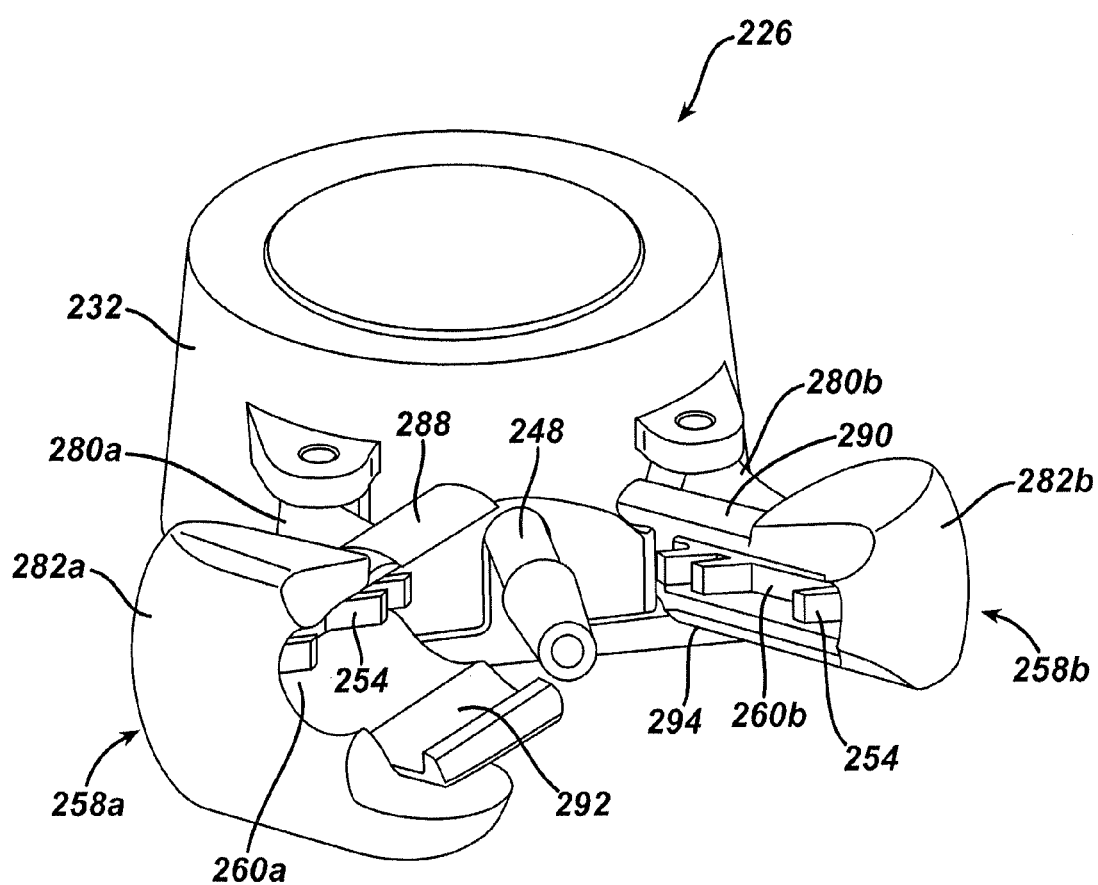
FIG. 15 depicts a perspective view of another exemplary alternative injection port having a two piece conduit retention sleeve with a trumpeted head portion, with the two sections of the retention sleeve in the open position.

First and second retention sleeve sections (158a, 158b) are pivotable between a closed position (see FIG. 12), and an open position where head portions (182a, 182b) are spaced away from each other. The open position of the first and second retention sleeve sections is essentially shown in FIG. 15 for a modified example of retention sleeve sections (258a, 258b) having a trumpeted (or flared) conduit passageway (286). When first and second retention sleeve sections (158a, 158b) are in their open position (FIG. 15) a fluid conduit (18) may be press fit over the distal end (150) of stem (148) until the end of the conduit abuts against distal end face (166) of port body (132). Thereafter, first and second retention sleeve sections (158a, 158b) are moved to their closed position shown in FIG. 14 and locked in this position (as further described herein).

When first and second retention sleeve sections (158a, 158b) are moved to their closed position (FIG. 12 and FIG. 14), they matingly engage one another so as to surround stem (148) and the portion of a fluid conduit (18) mounted to stem (148). An annular space is provided between the outer circumference of stem (148) and the interior sidewalls (160a, 160b) of first and second retention sleeve sections (158a, 158b). A fluid conduit (18) mounted to stem (148) will be located within this annular space. It should also be noted that, in the example shown in FIGS. 12-14, head portions (182a, 182b) extend beyond distal end (150) of stem (148) when the retention sleeve sections (158a, 158b) are in the closed position. In addition, the inner diameter D of the passageway (186) provided between head portions (182a, 182b) is greater than the outer diameter of distal end (150) of stem (148) as well as the distance between sidewalls (160a, 160b) (i.e., the inner diameter of the annular space surrounding stem (148) when the sleeve sections are in the closed position). Such a configuration may help prevent kinking of a fluid conduit (18) mounted on stem (148).

Like the example shown in FIGS. 5-11, first and second retention sleeve sections (158a, 158b) include cantilevered, flexible fingers (154). In the present example, three cantilevered fingers (154) are provided on each sleeve section (158a, 158b), and extend away from interior sidewalls (160a, 160b). However, any number of fingers (154) may be provided on each sleeve section (158a, 158b). It should also be understood that, in some versions, just one sleeve section (158a or 158b) has fingers (154). In some such versions, the other sleeve section (158a or 158b) may have recesses, a flat inner surface, and/or any other suitable features/configurations instead of having fingers (154). In the present example, cantilevered fingers (154) are sized and located such that, when sleeve sections (158a, 158b) are locked in the closed position, the free distal end walls (156) of the fingers (154) are positioned adjacent stem (148) and will be pressed against a fluid conduit (18) mounted on stem (148) in the manner described previously for the example shown in FIGS. 5-11. In the closed position, a pair of fingers (154) on each sleeve section are located adjacent stem (148) proximate to barb (152) (i.e., between barb (152) and port body (132)), while the third finger (154) on each sleeve section is located adjacent barb (152). Of course, a variety of other finger arrangements may be provided.

Cantilevered fingers (154) are also angled rearwardly towards the proximal end of retention sleeve sections (158a, 158b) such that, when sleeve sections (158a, 158b) are locked in the closed position shown in FIG. 14, fingers (154) are angled inwardly toward port body (132). Fingers (154) are angled similarly to fingers (54) in the previously-described example. The cantilevered fingers (154) on each sleeve section (158a, 158b), in their undeflected state shown in FIG. 14, also extend away from sidewalls (160a, 160b) generally parallel to one another (i.e., the fingers (154) of the first sleeve section (158a) extend parallel to one another, and the fingers (154) of the second sleeve section (158b) extend parallel to one another).

As mentioned previously, after a fluid conduit (18) has been mounted on stem (148), the retention sleeve sections (158a, 158b) are pivoted to, and locked in their closed position shown in FIG. 14. The free distal end surfaces (156) of cantilevered fingers (154) will be urged against the outer surface of the fluid conduit (18), causing the fingers (154) to be resiliently deformed (i.e., flexed) inwardly toward their respective interior sidewalls (160a, 160b) and away from distal end (150) of stem (148). This inward deflection is similar to that shown in FIGS. 9-10 for the previous example, and causes the free distal end surfaces (156) of flexible fingers (154) to exert an opposing force against the outer surface of the fluid conduit (18). The force exerted by distal end surfaces (156) will press the conduit (18) against stem (148) and help prevent detachment of the conduit (18). Once again, fingers (154) are configured in terms of their length, width, thickness, resilience, and material so as to flex sufficiently to allow the retention sleeve sections (158a, 158b) to be readily closed about the conduit (18), while also exerting sufficient force against the outer surface of the conduit (18) to substantially resist detachment of the conduit (18) from stem (148).

Like the previous example, the free distal end surfaces (156) of fingers (154) may extend parallel to the longitudinal axis of stem (148) when the sleeve sections (158a, 158b) are in their closed position with fingers (154) in their undeformed state (FIG. 14) in the present example. Alternatively, distal end surfaces (156) may be angled slightly with respect to the longitudinal axis L of stem (148) such that, when sleeve sections (158a, 158b) are locked about a conduit (18) mounted to stem (148), fingers (154) will be deformed inwardly by the conduit (18) with the distal end surfaces (156) generally parallel to the longitudinal axis of stem (148) (as shown in FIG. 10).

Figure 11:
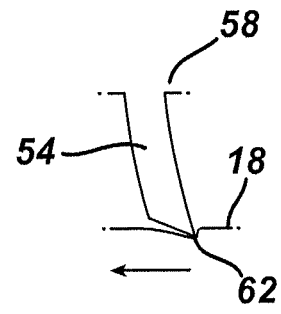
FIG. 11 depicts a schematic view of a cantilevered finger of the retention sleeve portion of the injection port of FIG. 5, where a force is being applied to the fluid conduit in the direction of the arrow.

As with the previous example, flexible fingers (154) of the present example not only help substantially retain a conduit (18) on stem (148) by exerting an opposing force against the conduit (18), they also retain the conduit (18) on stem (148) by substantially inhibiting movement of the conduit (18). When a force is exerted on a conduit (18) tending to pull the conduit (18) off of stem (148), friction between distal end surface (156) and the outer surface of the conduit (18) will result in fingers (154) being pulled in the same direction (e.g., away from port body (132)). As fingers (154) are pulled away from port body (132), the fingers (154) will be returned toward their undeformed state. This may result in the distal end surfaces (156) of fingers (154), particularly the trailing edges of distal end surfaces (156), being further urged against the outer surface of the fluid conduit (18), as shown in FIG. 11. Once again, the distal end surfaces (156), particularly the trailing edges thereof, may be configured to dig into the fluid conduit (18) to substantially resist conduit detachment while not damaging the conduit (e.g., angular or slightly rounded edges on distal end surfaces (156)).

First and second retention sleeve sections (158a, 158b) may be locked in their closed position in any of a variety of ways as will be apparent to one skilled in the art in view of the teachings herein. By way of example only, after sleeve sections (158a, 158b) are moved to their closed position (FIG. 14), a tubular collar (not shown) may be slid along the fluid conduit (18) and over the closed sleeve sections (158a, 158b). Such a collar may be tapered and made from a resilient material such that the collar may be tightly fit about the mated sleeve sections (158a, 158b) in order to lock the sleeve sections (158a, 158b) in their closed position. Alternatively, external threads may be provided on head portion (182a, 182b) of the retention sleeve such that an internally threaded collar may be threadably attached over the head portion (182a, 182b) in order to lock sleeve sections (158a, 158b) in their closed position. As yet another alternative, one or more pins or other connector elements may be provided on one or both of sleeve sections (158a, 158b), with the pins or connector elements lockingly received in aligned cavities or other openings in the opposite sleeve section.

Figure 16:
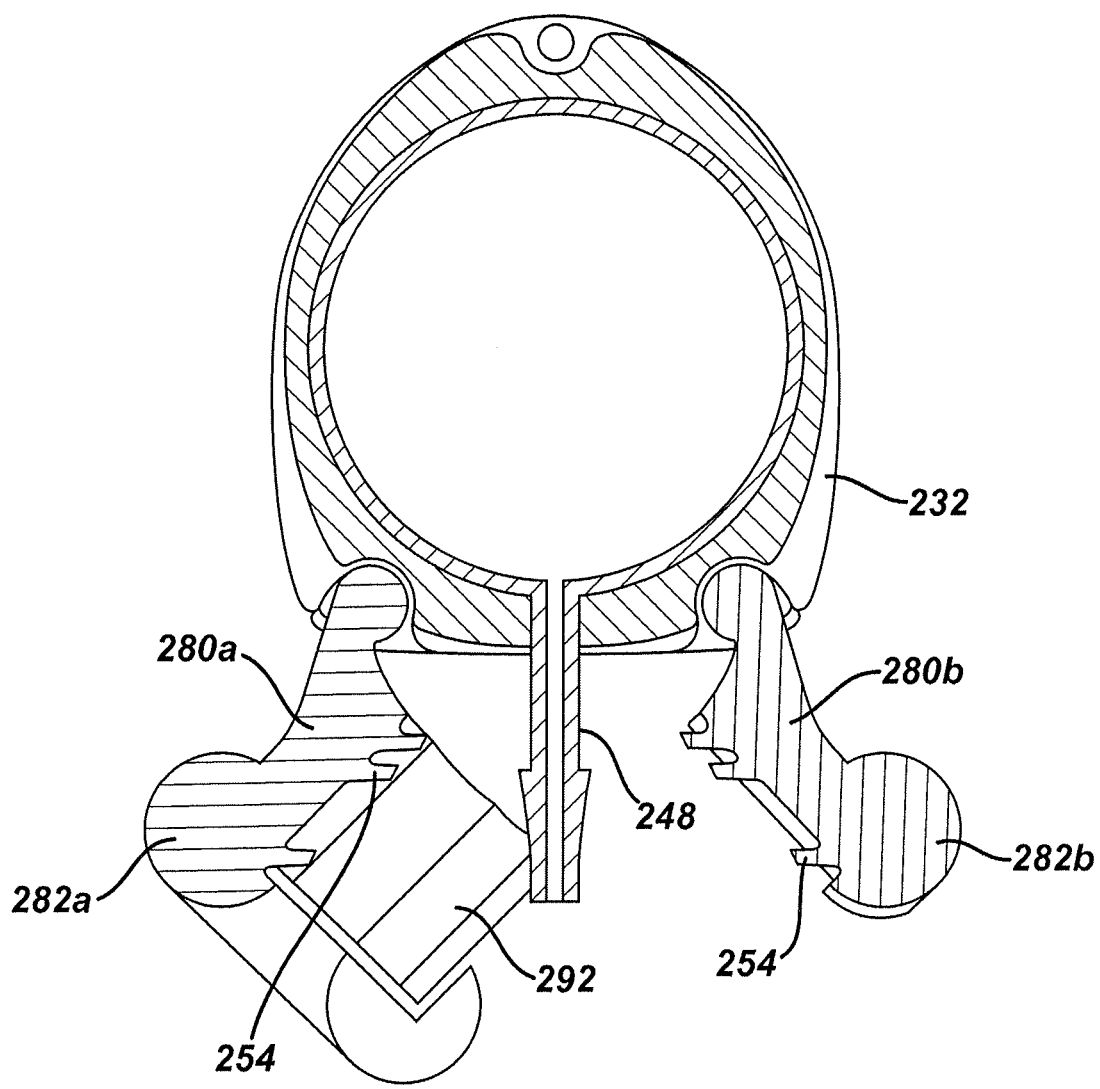
FIG. 16 depicts a top cross-sectional view of the injection port of FIG. 15, taken in a plane extending parallel to the bottom of the injection port along the longitudinal axis of the stem, with the two sections of the retention sleeve in an open position.
Figure 17:
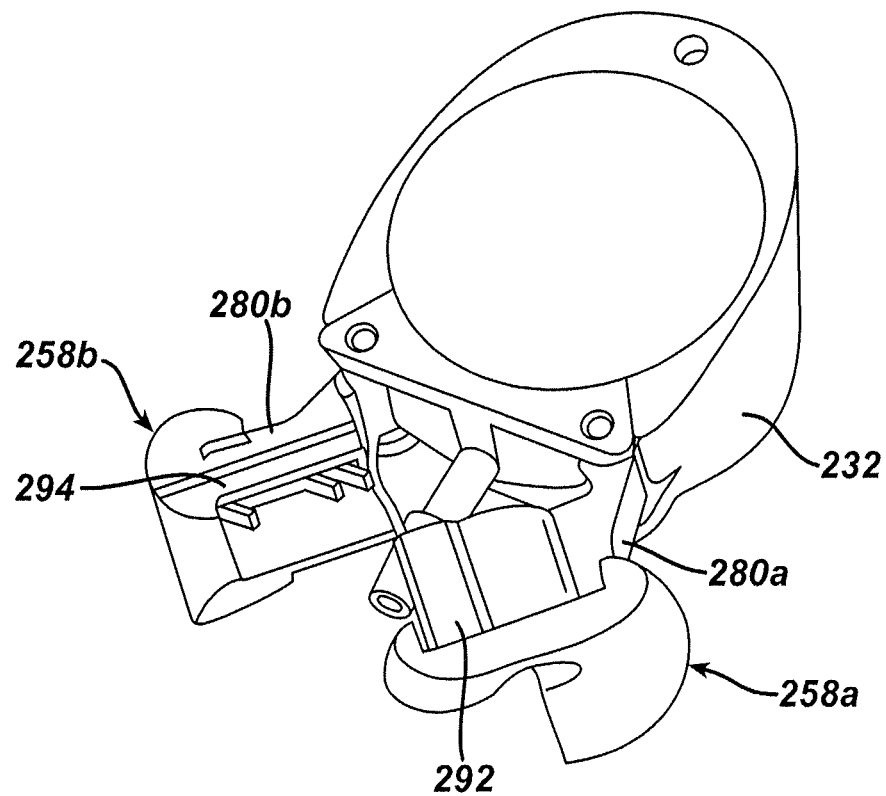
FIG. 17 depicts a bottom perspective view of the injection port of FIG. 15.

In the example shown, finger support section (180a) of the first retention sleeve section (158a) includes an arcuate upper coupling member (188) configured to matingly and lockingly engage an upper mounting rib (not shown) provided on finger support section (180b) of the second retention sleeve section (158b). Upper coupling member (188) snaps over, and locks to the upper mounting rib. The upper mounting rib is not visible in FIG. 12, however, the locking mechanism is further described below with respect to the modified example of FIGS. 15-17. In addition, a similar arcuate lower coupling member (not shown) is provided along the bottom of first retention sleeve section (158a), as well as a lower mounting rib (not shown) along the bottom of second retention sleeve section (158b).

FIGS. 15-18 depict another exemplary alternative implantable injection port (226) having a two piece conduit retention sleeve (258) configured to lock over a conduit (18) attached to the port (226). Port (226) is essentially constructed the same as port (126) described above, with the exception of the head portion (282) of the retention sleeve (258). Thus, injection port (226) includes first and second retention sleeve sections (258a, 258b) that are pivotally attached to the port housing (i.e., to port body (232)). Retention sleeve sections (258a, 258b) also include a plurality of cantilevered fingers (254) extending angularly away from inner sidewalls (260a, 260b).

Figure 18:
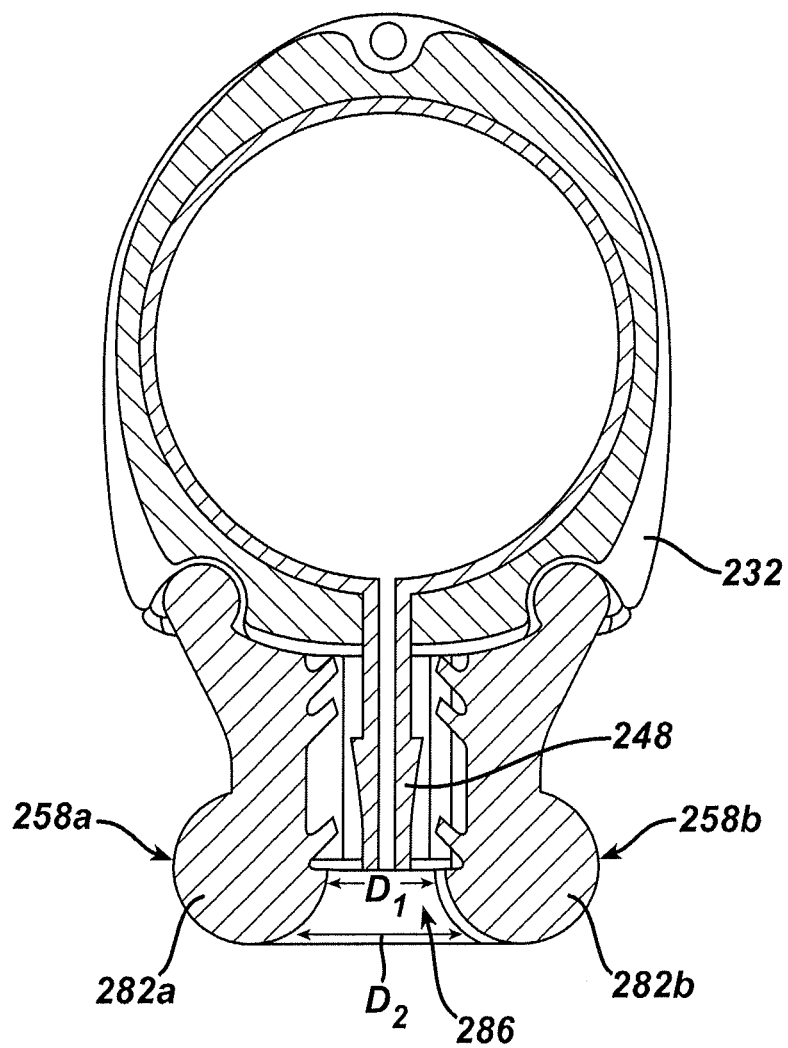
FIG. 18 depicts a top cross-sectional view of the injection port of FIG. 15, taken in a plane extending parallel to the bottom of the injection port along the longitudinal axis of the stem, with the two sections of the retention sleeve in a closed position.

Head portions (282a, 282b) of first and second retention sleeve sections (258a, 258b) differ from the head portions of the previous example in that, when the retention sleeve sections (258a, 258b) are matingly and lockingly engaged, the conduit passageway (286) (see FIG. 18) provided between the head portions (282a, 282b) is trumpeted (or flared) rather than having a constant diameter D (as shown in FIG. 12). In particular, the diameter of the passageway increases exponentially in the distal direction (i.e., the direction extending away from port body (232)). Thus, as shown in FIG. 18 where the sleeve sections (258a, 258b) are in their closed position, diameter D2 of passageway (286) is greater than diameter D1 of passageway (286) nearer to the proximal end of stem (248). The trumpeting (or flaring) of the passageway (286) provided between head portions (282a, 282b) may help to further substantially prevent kinking of a flexible conduit attached over stem (248). It should be pointed out that the diameter of trumpeted passageway (286) may increased linearly in the distal direction, rather than exponentially, or increase in some other manner.

FIGS. 15-18 also depict the manner in which first retention sleeve section (258a) is locked to second retention sleeve section (258b). This same locking arrangement is provided in the previous example of FIGS. 12-14. In particular, finger support section (280a) of the first retention sleeve section (258a) includes an arcuate upper coupling member (288) configured to matingly and lockingly engage an upper mounting rib (290) provided on finger support section (280b) of the second retention sleeve section (258b). Upper coupling member (288) is shaped so that as first and second retention sleeve sections (258a, 258b) are moved toward their closed position, upper coupling member (288) initially will be deformed upwardly by upper mounting rib (290). As the retention sleeve sections (258a, 258b) are further urged to their closed position, upper coupling member (288) will snap back to its undeformed position over upper mounting rib (290), thus substantially locking first and second retention sleeve sections (258a, 258b) to one another. Similarly, an arcuate lower coupling member (292) is provided along the bottom of first retention sleeve section (258a), as well as a mating lower mounting rib (294) along the bottom of second retention sleeve section (258b). When first and second retention sleeve sections (258a, 258b) are moved to their closed position, lower coupling member (292) will resiliently snap over lower mounting rib (294), thus further locking first and second retention sleeve sections (258a, 258b) to one another.

As with the example shown in FIGS. 12-14, the example shown in FIGS. 15-18 may include a collar that slides over sleeve sections (258a, 258b) to further substantially secure closed sleeve sections (258a, 258b) to each other. As yet another merely illustrative variation, an injection port may have substantially straight sleeve sections like those shown in FIGS. 12-14, and a bell-shaped collar may be slid at least partially over such sleeve sections when such sleeve sections are in a closed position. Such a bell-shaped collar may thus substantially secure the closed sleeve sections to each other and may also provide a substantially trumpeted passageway in a manner similar to that provided by head portions (282a, 282b). Furthermore, even an injection port having an integral sleeve section such as injection port (26) shown in FIGS. 5-11 may have a trumpeted passageway. Still other suitable components, features, and configurations will be apparent to those of ordinary skill in the art in view of the teachings herein.

While previously-described examples included a two-piece retention sleeve pivotally attached to the port housing, a variety of other arrangements will be apparent to those skilled in the art in view of the teachings herein. For example, the first and second retention sleeve sections may be slidably attached to the port housing, rather than being pivotally attached. In some such versions, after the fluid conduit is press fit over the stem, the first and second retention sleeve sections may be slid against the conduit from either side and locked into position. As yet another merely illustrative alternative, first and second retention sleeve sections may be configured to not only lock together about the fluid conduit, but also to be attachable to the port housing. Thus, after the fluid conduit is press fit over the stem, the first and second retention sleeve sections may be brought together over the fluid conduit and locked to one another and secured to the port housing (e.g., by means of a locking fastener arrangement, snap fitting, etc.).

As mentioned previously, the injection ports described herein may be used as part of a gastric band system. By way of example, a gastric band is positioned in a patient in the manner described previously, and an injection port of the type described herein also implanted in the patient. One end of a fluid conduit is attached to the injection port, such as by mounting one end of the conduit over the injection port stem, and then fitting the retention sleeve attached to the housing over at least a portion of the conduit mounted to the stem such that the flexible fingers in the retention sleeve help prevent the conduit from being pulled off of the stem. The other end of the conduit is coupled to the gastric band in order to provide fluid communication between the gastric band and the reservoir of the injection port. The conduit may be coupled to the injection port and/or the gastric band either before or after those structures are implanted in the patient.

As yet another example, gastric band system (10) may include an implanted pump/reservoir system (not shown) instead of including an injection port (12). Such a pump/reservoir system may be controlled to selectively vary the amount of fluid in gastric band (20). Examples of such a system are described in U.S. Pat. No. 7,390,294, entitled "Piezo Electrically Driven Bellows Infuser for Hydraulically Controlling an Adjustable Gastric Band," issued Jun. 24, 2008, the disclosure of which is incorporated by reference herein. Other examples of such a system are described in U.S. Pat. No. 7,351,240, entitled "Thermodynamically Driven Reversible Infuser Pump for Use as a Remotely Controlled Gastric Band," issued Apr. 1, 2008, the disclosure of which is incorporated by reference herein. Such systems may include a catheter or other type of conduit coupling the pump/reservoir with gastric band (20). Accordingly, such systems may include any of the various conduit/catheter retention features described herein. Similarly, it should be understood that gastric band (20) may include any of the various conduit/catheter retention features described herein. Various suitable ways in which the conduit/catheter retention features described herein may be incorporated into a pump/reservoir and/or into a gastric band (20) will be apparent to those of ordinary skill in the art in view of the teachings herein.

It should be understood from the foregoing that conduit/catheter retention features such as those described herein may be incorporated into virtually any type of implanted device. The above described examples of gastric band systems are mere illustrations. The inventors' contemplation is not limited to components of gastric band systems. By way of example only, conduit/catheter retention features may be incorporated into an implanted drug infusion port, chemotherapy port, or any other type of implantable port that is used to deliver medication. Still other types of implanted devices that may incorporate conduit/catheter retention features will be apparent to those of ordinary skill in the art in view of the teachings herein.

It will become readily apparent to those skilled in the art that examples described herein may have applicability to other types of implantable bands. For example, bands are used for the treatment of fecal incontinence. One such band is described in U.S. Pat. No. 6,461,292, entitled "Anal Incontinence Treatment with Wireless Energy Supply," issued Oct. 8, 2002, the disclosure of which is incorporated by reference herein. Bands can also be used to treat urinary incontinence. One such band is described in U.S. Pat. No. 7,621,863, entitled "Urinary Incontinence Treatment with Wireless Energy Supply," issued Nov. 24, 2009, the disclosure of which is incorporated by reference herein. Bands can also be used to treat heartburn and/or acid reflux. One such band is described in U.S. Pat. No. 6,470,892, entitled "Mechanical Heartburn and Reflux Treatment," issued Oct. 29, 2002, the disclosure of which is incorporated by reference herein. Bands can also be used to treat impotence. One such band is described in U.S. Pat. No. 7,442,165, entitled "Penile Prosthesis," issued Oct. 28, 2008, the disclosure of which is incorporated by reference herein. Various ways in which the teachings herein may be incorporated with the teachings of these patent references will be apparent to those of ordinary skill in the art.

Versions of the present invention have application in conventional endoscopic and open surgical instrumentation as well as application in robotic-assisted surgery.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometries, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

I claim:

1. A surgically implantable medical port, comprising:
   (a) a housing having a fluid reservoir therein;
   (b) a tubular stem extending away from the housing, the tubular stem having a hollow interior and a distal end, wherein the interior of the stem is in fluid communication with the reservoir;
   (c) a resilient fluid conduit received over the distal end of the stem;
   (d) a retention sleeve, wherein the retention sleeve comprises a plurality of retention sleeve portions, wherein the retention sleeve portions are pivotably attached to the housing, and wherein the retention sleeve portions are configured to close about a portion of the tubular stem; and
   (e) a plurality of cantilevered fingers, each finger having a respective free end, wherein the fingers extend from an interior surface of at least one retention sleeve portion of the plurality of retention sleeve portions, and wherein the fingers are mounted with respect to the stem such that the free ends of the fingers urge the fluid conduit against the stem.

2. The medical port of claim 1, wherein the cantilevered fingers extend away from the interior surface of the retention sleeve portions, and are angled toward the housing, such that the free ends of the fingers resist movement of the conduit away from the housing.

3. The medical port of claim 2, wherein the retention sleeve comprises first and second mating retention sleeve portions.

4. The medical port of claim 3, wherein the first retention sleeve portion is snap fit to the second retention sleeve portion.

5. The medical port of claim 1, wherein the retention sleeve includes a head portion having a trumpeted passageway, wherein the fluid conduit extends through the trumpeted passageway.

6. The surgically implantable medical port of claim 1, wherein the housing comprises a feature configured to receive a suture for securing the housing to tissue.

7. The surgically implantable medical port of claim 1, further comprising a gastric band having an inflatable member coupled to the fluid conduit, wherein the reservoir, fluid conduit, and the inflatable member together form a closed fluid circuit.

8. A surgically implantable injection port, comprising:
   (a) a housing;
   (b) a fluid reservoir defined in part by the housing;
   (c) a needle penetrable septum having an outer surface, wherein the septum defines part of the fluid reservoir such that the reservoir is configured to receive part of a needle inserted through the outer surface of the septum;

(d) a tubular stem extending away from the housing, the tubular stem having a hollow interior and a distal end, wherein the interior of the stem is in fluid communication with the reservoir, wherein the tubular stem is configured to receive a resilient fluid conduit;

(e) a retention sleeve configured to extend about at least a portion of a fluid conduit received by the tubular stem, the retention sleeve having an interior, the retention sleeve being secured relative to the housing, and wherein the retention sleeve comprises first and second sections attached to the housing and matingly secured to one another; and (f) a plurality of flexible fingers having respective free ends, wherein the fingers extend angularly away from the interior of the retention sleeve and toward the tubular stem, wherein the fingers are configured to extend into a fluid conduit received by the tubular stem such that the free ends of one or more of the fingers are urged against the outer surface of a fluid conduit received by the tubular stem, and wherein the plurality of flexible fingers comprises a first set of fingers cantilevered from an inner surface of the first section of the retention sleeve and a second set of fingers cantilevered from an inner surface of the second section of the retention sleeve, and wherein the free ends of the first and second set of fingers are configured to urge against opposite sides of the outer surface of a fluid conduit received by the tubular stem.

9. The injection port of claim 8, wherein the stem includes a barb located between the distal end of the stem and the housing, and further wherein each of the first and second sets of fingers includes at least one finger having a free end configured to urge against a fluid conduit received by the tubular stem at a location between the barb and the housing, wherein each of the first and second sets of fingers includes at least one finger having a respective free end configured to urge against a fluid conduit received by the tubular stem at a location adjacent the barb.

10. The injection port of claim 8, wherein the retention sleeve includes a head portion having a trumpeted passageway, wherein the head portion is configured such that a fluid conduit received by the tubular stem extends through the trumpeted passageway.

11. The injection port of claim 8, further comprising a fluid conduit coupled with the tubular stem and a gastric band having an inflatable member coupled to the fluid conduit, wherein the reservoir, fluid conduit, and the inflatable member together form a closed fluid circuit.

12. A method of attaching a fluid conduit to an implantable medical port, wherein the medical port comprises a housing having a fluid reservoir, a tubular stem extending away from the housing, the tubular stem having a hollow interior and a distal end, wherein the interior of the stem is in fluid communication with the reservoir, and a retention sleeve, wherein the retention sleeve comprises first and second sections attached to the housing and wherein the retention sleeve further comprises a first and second set of fingers having respective free ends, wherein the first set of the fingers are cantilevered from an inner surface of the first section of the retention sleeve, wherein a second set of the fingers are cantilevered from an inner surface of the second section of the retention sleeve, and wherein the first and second sections are movable between open and closed positions, the method comprising: (a) mounting one end of the fluid conduit over the distal end of the stem with the first and second sections of the retention sleeve in the open position; and (b) fitting the retention sleeve attached to the housing over at least a portion of the conduit mounted on the stem, wherein the act of fitting the retention sleeve over at least a portion of the conduit comprises moving the first and second sections of the retention sleeve to the closed position such that when the retention sleeve is fitted over the conduit the free ends of the first and second sets of fingers are urged against the fluid conduit on opposite sides thereof; wherein, when the retention sleeve is fitted over the conduit, the flexible fingers are deformed by the conduit such that the free ends of the fingers press against the fluid conduit in order to retain the conduit on the stem.

13. The method of claim 12, wherein the first and second sections lockingly engage one another when moved to the closed position.

14. The method of claim 12, further comprising the steps of positioning a gastric band in a patient, positioning the medical port in the patient, and coupling an end of the conduit to the gastric band to provide fluid communication between the gastric band and the reservoir of the injection port.

* * * * *